United States Patent [19]

Bernard et al.

[11] 4,104,320

[45] Aug. 1, 1978

[54] METHOD OF DEHYDROCYCLIZING ALIPHATIC HYDROCARBONS

[75] Inventors: Jean René Bernard, St-Symphorien sur Ozon; Jean Nury, Caluire, both of France

[73] Assignee: Elf-Union, Paris, France

[21] Appl. No.: 718,584

[22] Filed: Aug. 30, 1976

[30] Foreign Application Priority Data

Sep. 10, 1975 [FR] France .................. 75 27781

[51] Int. Cl.² .................. C07C 15/02; B01J 29/28
[52] U.S. Cl. .................. 260/673.5; 208/138; 208/141; 260/668 B; 260/673; 423/328
[58] Field of Search .............. 260/673.5, 673, 668 D; 208/137, 138, 140, 141; 423/328, 329; 252/455 Z

[56] References Cited

U.S. PATENT DOCUMENTS

| 3,130,006 | 4/1964 | Rabo et al. | 423/328 |
|---|---|---|---|
| 3,140,253 | 7/1964 | Plank et al. | 208/120 |
| 3,216,789 | 11/1965 | Breck et al. | 423/328 |
| 3,367,885 | 2/1968 | Rabo et al. | 252/455 |
| 3,819,507 | 6/1974 | Oishi | 208/139 |
| 3,830,724 | 8/1974 | Schutt | 208/111 |
| 3,864,283 | 2/1975 | Schutt | 208/111 X |
| 3,890,218 | 6/1975 | Morrison | 208/135 |
| 3,904,738 | 9/1975 | Robson | 423/328 |

*Primary Examiner*—Delbert E. Gantz
*Assistant Examiner*—G. E. Schmitkons
*Attorney, Agent, or Firm*—Flynn & Frishauf

[57] ABSTRACT

This invention relates to a method of dehydrocyclizing aliphatic hydrocarbons to form corresponding aromatic hydrocarbons. According to the invention, a batch of aliphatic hydrocarbons, in the presence of hydrogen at a temperature of 430° to 550° C is passed over a catalyst consisting essentially of a type L zeolite having exchangeable cations of which at least 90% are alkali metal ions selected from the group consisting of ions of sodium, lithium, potassium, rubidium and caesium and containing at least one metal selected from the group which consists of metals of groups VIII of the periodic table of elements, tin and germanium, said metal or metals including at least one metal from group VIII of said periodic table having a dehydrogenating effect, so as to convert at least part of the batch into aromatic hydrocarbons. The aliphatic hydrocarbons preferably contain 6 – 10 carbon atoms.

25 Claims, No Drawings

METHOD OF DEHYDROCYCLIZING ALIPHATIC HYDROCARBONS

The invention relates to a method of dehydrocyclising aliphatic hydrocarbons, more particularly batches of hydrocarbons comprising paraffins containing 6 to 10 carbon atoms, to form the corresponding aromatic hydrocarbons.

This reaction, called "reforming," is conventionally used in the oil industry for converting normal paraffins (which are undesirable constituents in petrol owing to their very low octane number) into aromatic components having a high octane number, which are suitable as fuels and also have many other petrochemical uses, e.g. as solvents, etc.

The conventional methods of performing these dehydrocyclisation reactions are based on the use of catalysts comprising a noble metal on a carrier. Known catalysts of this kind are based on alumina carrying from 0.2 to 0.8% by weight of platinum and a second auxiliary metal.

The possibility of using carriers other than alumina has also been studied and it has been proposed to use certain molecular sieves such as X and Y zeolites, which are suitable provided that the reactants and products are sufficiently small to flow in the pores of the zeolite.

In the conventional method of carrying out the aforementioned dehydrocyclisation, a batch of hydrocarbons to be converted is passed over the catalyst, in the presence of hydrogen, at temperatures of the order of 500° C and pressures varying from 5 to 30 bars. Part of the injected batch is converted into aromatic hydrocarbons by dehydrocyclisation, but the reaction is accompanied by isomerization and cracking reactions which also convert the paraffins into isoparaffins and lighter hydrocarbons.

The rate of conversion of the hydrocarbon batch into aromatic hydrocarbons varies with the reaction conditions and the nature of the catalyst.

The catalysts hitherto used have given satisfactory results but it has been discovered that catalysts based on L zeolite are more selective with regard to the dehydrocyclisation reaction and can be used to improve the rate of conversion to aromatic hydrocarbons without requiring higher temperatures and lower pressures, which usually have a considerable adverse effect on the stability of the catalyst.

To this end, the invention provides a method of dehydrocyclising aliphatic hydrocarbons, characterised in that a batch of the hydrocarbons is contacted in the presence of hydrogen at a temperature of 430° - 550° C with a catalyst consisting essentially of a type L zeolite having exchangeable cations of which at least 90% are alkali metal ions selected from the group consisting of ions of sodium, lithium, potassium, rubidium and caesium and containing at least one metal selected from the group which consists of metals of group VIII of the periodic table of elements, tin and germanium, said metal or metals including at least one metal from group VIII of said periodic table having a dehydrogenating effect, so as to convert at least part of the batch into aromatic hydrocarbons.

In this method, the use of L zeolite-based catalysts is very advantageous since these catalysts are very efficient with regard to dehydrocyclisation and are both more selective and more stable than known catalysts.

In the method according to the invention, the batch of hydrocarbons preferably comprises paraffins containing 6 to 10 carbon atoms, preferably normal paraffins.

This hydrocyclisation is carried out in the presence of hydrogen at a pressure adjusted so as to favour the reaction thermodynamically and limit undesirable hydro-cracking reactions by kinetic means. The pressures used vary from 0 to 40 bars, preferably from 0 to 25 bars, the molar ratio of hydrogen to hydrocarbons being between 2 to 20, preferably between 3 and 10.

In the temperature range from 430° to 550° C the dehydrocyclisation reaction occurs with acceptable speed and selectivity.

If the operating temperature is below 430° C, the reaction speed is insufficient and consequently the yield is too low for industrial purposes. When the operating temperature is high, approximately 550° C, and although the speed of the dehydrocyclisation reaction is high, interfering secondary reactions such as hydrocracking and coking occur, and substantially reduce the yield. It is not advisable, therefore, to exceed the temperature of 550° C.

The preferred temperature range (450° - 550° C) is that in which the process is optimum with regard to activity, selectivity and the stability of the catalyst.

The hourly liquid spatial velocity of the hydrocarbons, in accordance with the feed rate, is between 0.1 and 20 $h^{-1}$, preferably between 1 and 4.

The catalyst according to the invention is a type L zeolite charged with one or more dehydrogenating constituents.

L type zeolites are synthetic zeolites such as chabazite and crystallise in the hexagonal system. A theoretical formula is $M_{9/n}[(AlO_2)_9(SiO_2)_{27}]$ in which M is a cation having the valency $n$.

The real formula may vary without changing the crystalline structure; for example the ratio of silicon to aluminium may vary from 2.5 to 3.5.

A more complete description of these zeolites is given e.g. in U.S. Pat. No. 3,216,789 which, more particularly, gives a conventional description of these zeolites with respect to their X-ray diffraction spectrum. The zeolites occur in the form of cylindrical crystals a few hundred Angstroms in diameter and have channel-shaped pores.

The hydrocarbon sorption pores are channels parallel to the cylinder axis and between 7 and 8 Å in diameter.

L zeolites are conventionally synthesized in the potassium form — i.e. in the theoretical formula given previously, most of the M cations are potassium. The M cations are exchangeable, so that a given L zeolite, e.g. an L zeolite in the potassium form, can be used to obtain L zeolites containing other cations, by subjecting the L zeolite to ion exchange treatment in an aqueous solution of appropriate salts. However, it is difficult to exchange more than 80% of the original cation, e.g. potassium, since some exchangeable cations in the zeolite are in sites which are difficult for the reagents to reach.

In the method according to the invention, the catalyst carrier is advantageously an L zeolite in which at least 90% of the exchangeable cations are ions of at least one alkali metal chosen from the group comprising potassium, lithium, sodium, rubidium and caesium.

In a preferred embodiment, an L zeolite is used in which the exchangeable cations comprise, for example, caesium ions and/or rubidium ions. In the latter case, the caesium and/or rubidium ions preferably make up at least 30% of the exchangeable cations of the L zeolite.

As previously explained, an L zeolite of the aforementioned kind can be obtained from an L zeolite in the potassium form by subjecting it to ion exchange by treatment with an aqueous solution containing a rubidium or caesium salt, after which the zeolite is washed so as to eliminate excess ions.

The rate of exchange can be increased by repeated ion exchange treatment of the zeolite. Since, however, it is difficult to exchange more than 80% of the original cation in the final product, the process yields an L zeolite in which at least 90% of the exchangeable cations are potassium ions and rubidium or caesium ions.

The generally accepted theory relating to the dehydrocylisation of paraffins refers to acid sites in which the olefins formed by dehydrogenation of paraffins are cyclised. By contrast, in the method according to the invention, the L zeolites used are neutral, i.e. have not been exchanged with either hydrogen or ammonium ions capable of producing hydrogen ions or with multivalent cations which make zeolites somewhat acid.

The catalyst carriers according to the invention are charged with one or more dehydrogenating constituent metals from group VIII of the periodic table of elements, e.g. nickel, ruthenium, rhodium, palladium, iridium or platinum.

The preferred substances are palladium and particularly platinum, which are more selective with regard to dehydrocyclisation and are also more stable under the dehydrocyclisation treatment conditions.

The preferred percentage of platinum in the catalyst is between 0.1 and 1.5%, the lower limit corresponding to minimum catalyst activity and the upper limit to maximum activity; this allows for the high price of platinum, which does not justify using a higher quantity of the metal since the result is only a slight improvement in catalyst activity.

In order to improve the stability of the catalyst, another metal such as rhenium, iridium, tin or germanium is preferably introduced at the same time as platinum and/or palladium, the quantity of the other metal being such that the total percentage of metals in the zeolite is from 0.1 to 1.5% by weight. In this manner a reduction can also be made in the percentage of platinum or palladium without affecting the activity of the catalyst.

Metals are introduced into the L zeolite by impregnation or exchange in an aqueous solution of appropriate salt. When it is desired to introduce two metals into the zeolite, the operation is carried out simultaneously, using a solution of salts of both metals.

By way of example, platinum can be introduced by impregnating the zeolite with an aqueous solution of chloroplatinic acid, choroplatinuous acid, dinitrodiamino-platinum or tetramminoplatinum chloride. In an ion exchange process, platinum can be introduced by using cationic platinum complexes such as tetramminoplatinum chloride.

Similar compounds can be used for iridium, and perrhenic acid for rhenium.

After the desired metal or metals have been introduced, the catalyst is calcined in air and then reduced in hydrogen.

At this stage it is ready for use in the dehydrocyclisation process. In some cases however, for example when the metal or metals have been introduced by an ion exchange process, it is preferably to eliminate any residual acidity of the zeolite by heating the catalyst with an aqueous solution of an alkaline base such as sodium carbonate in order to neutralise any hydrogen ions formed during the reduction of metal ions by hydrogen.

In other cases, the catalyst can be sulphurated so as to reduce the hydro-cracking reactions, which are always more prominent at the beginning of the hydrocyclisation.

By way of example, a catalyst based on L zeolite in the potassium form containing 0.9% platinum was prepared as follows:

5 g of L zeolite in the potassium form was calcined at 480° C for 3 hours. The resulting solid was impregnated with a solution of 0.09 g diammino platinum chloride in 5 ml water.

The impregnated solid was left at ambient temperature for 30 minutes, then dried in an oven at 100° C.

The resulting catalyst was calcined for 3 hours at 480° C in a stream of dry air. It was found by analysis to contain 0.5% platinum.

It was then placed in a dynamic catalytic reactor and reduced in a stream of hydrogen at 510° C.

If it is desired to neutralize the residual acidity of the zeolite, the catalyst after reduction is processed with 50 ml of 0.1 N sodium carbonate at 50° C for 24 hours.

As a second example, a catalyst containing platinum and comprising rubidium or caesium as the exchangeable cation of the zeolite was prepared as follows: 10 g of L zeolite in the potassium form was contacted with 100 ml of a solution containing 2 mols pf rubidium chloride per liter. The mixture was agitated and boiled for 3 hours; the solid was then filtered and washed until the chloride ions had disappeared. The operation was repeated once.

An L zeolite containing caesium can be obtained simply by using caesium chloride instead of rubidium chloride in the preceding process. In the case of rubidium, the carrier contains 21% by weight of the metal; in the case of caesium, it contains 23% by weight of the last-mentioned alkaline metal. The rates of exchange are 70% and 49% respectively; the remaining cations are the original potassium.

The resulting carriers are impregnated with an aqueous solution of tetramminoplatinum chloride so as to deposit 0.6% by weight of platinum. The mixture is left to mature at ambient temperature for 30 minutes, after which the catalyst is dried in an oven at 110° C and finally calcined for 3 hours at 480° C in a stream of dry air.

The previously-described catalysts can be used for dehydrocyclising any batch of hydrocarbons containing paraffins with 6 – 10 carbon atoms, more particularly normal paraffins and isoparaffins containing a straight chain of at least 6 carbon atoms.

The dehydrocyclisation reaction is carried out by injecting one of the batches in the presence of hydrogen into a dynamic reactor after the chosen catalyst has been introduced therein.

The invention will be more clearly understood from the following non-limitative examples which are given so as to illustrate the method according to the invention, applied to the dehydrocyclisation of normal hexane.

EXAMPLES 1 to 6

In these examples, a dynamic reactor was used at atmospheric pressure. In all the examples, 0.6 g of catalyst was placed in the reactor and reduced at 510° C in a stream of hydrogen. Next, a mixture of normal hexane and hydrogen was sent over the catalyst, the molar ratio of hydrogen to N-hexane being 6. The total hourly spatial velocity of the gases was 1500 $h^{-1}$. After the catalyst had been in operation for an hour, the hydrocarbon effluents were analysed by flame ionization chromatography. The conditions and results of examples 1 to 6 are shown in Table 1, in which the last 4 columns represent the percentages by weight of hydrocarbons in the analysed effluents. In the columns, "light products" denote hydrocarbons containing less than 6 carbon atoms and branched isomers of hexane; "hexanes" denote not only $C_6$ olefins but also methylcyclopentane. The "aromatics" mainly consist of benzene.

TABLE I

| Ex. | Catalyst | Temp. °C | % n Hexane | % Light Products | % Hexanes | % Aromatics |
|---|---|---|---|---|---|---|
| 1 | 0.9% Pt/KL prepared by impregnation | 490° C | 2.2 | 4.09 | 1.6 | 92.2 |
| 2 | " | 460° C | 47.1 | 3.4 | 9.25 | 40.3 |
| 3 | 0.8% Pt/KL prepared by exchange | 460° C | 52 | 7.8 | 4.2 | 36 |
| 4 | " Treatment with 0.1 N NaHCO₃ after reduction | 460° C | 50.1 | 2.1 | 8.3 | 38.8 |
| 5 | 0.3% Pt, 0.05% Ir/KL prepared by impregnation | 460° C | 53 | 2.1 | 8.6 | 36.3 |
| 6 | 0.8% Pt/NaL prepared by impregnation | 460° C | 39.3 | 3.8 | 7.2 | 55.7 |

The catalysts in Examples 1 and 2 were an L zeolite in the potassium form containing 0.9% platinum and were prepared by impregnation.

The catalyst in Example 3 was a zeolite in the potassium form containing 0.8% platinum fixed by ionic exchange.

The catalyst in Example 4 was identical with the catalyst in Example 3 except that after being reduced with hydrogen it was neutralized with a solution of 0.1 N sodium carbonate.

The catalyst in Example 5 was an L zeolite in the potassium form containing 0.3% platinum and 0.05% iridium fixed by impregnation.

The catalyst in Example 6 was an L zeolite in the potassium form exchanged with sodium (i.e. containing 2.2 by weight of sodium and 13.1% by weight of potassium) and containing 0.8% platinum fixed by impregnation.

The results show the efficiency of the catalyst, which gives good n-hexane conversion rates at temperatures below 500° C with considerable selectivity for the dehydrocyclisation reaction.

EXAMPLE 7

30 g of the catalyst used in Example 1 was placed in a metal dynamic reactor and reduced at 510° C with hydrogen. A batch of normal hexane and hydrogen, the molar ratio of n-hexane to hydrogen being 6, was sent over the catalyst at a pressure of 10 bars and a liquid hourly spatial velocity of 2.5. When the catalyst activity was stable, the conversion of n-hexane at 500° C was 80% and the reaction products contained 21% light products, 29% n-hexane isomers and 50% aromatics.

EXAMPLES 8 – 10

In these examples, a dynamic reactor was used at atmospheric pressure. In all the examples, 0.6 g of catalyst was placed in the reactor and reduced at 510° C in a stream of hydrogen. Next, a mixture of normal hexane and hydrogen, the molar ratio of hydrogen to n-hexane being 6, was sent over the catalyst. The total hourly spatial velocity of the gases was 1500 $h^{-1}$, and the temperature was 460° C. After the catalyst had been in operation for an hour, the hydrocarbon effluents were analysed by flame ionisation chromatography.

The reseults of Examples 8 – 10 are shown in Table 2. In this Table, conversion is defined by the percentage by weight of hydrocarbons other than n-hexane in the gaseous effluents, and the selectivity is defined by the percentages by weight of hydrocarbons obtained in the converted product. The light products are defined as saturated $C_1$ – $C_5$ hydrocarbons and $C_2$ – $C_4$ olefins.

The isohexanes are methylpentanes. The same fraction contains $C_5$ olefins.

The intermediates comprise $C_6$ olefins and methylcyclopentane.

The aromatics mainly comprise benzene, but also contain traces of toluene and xylene.

A comparison of the results in Examples 8 – 10 shows that catalysts based on L zeolite containing rubidium or caesium are more active and more selective than catalysts based on L zeolite in the potassium form.

TABLE 2

| | | | Selectivity | | | |
|---|---|---|---|---|---|---|
| Examples | Catalyst | Conversion | Light Products | i-Hexane | Intermediates | Aromatics |
| 8 | 0.6% Pt/KL. | 50 | 3 | 5 | 13 | 79 |
| 9 | 0.6% Pt/0.7 Rb.0.3 KL | 73 | 3 | 5 | 6 | 88 |
| 10 | 0.6% Pt/0.49 Cs.0.51 KL | 71 | 2 | 5 | 8 | 85 |

We claim:

1. A method of dehydrocyclizing non-cyclic aliphatic hydrocarbons, characterised in that in the presence of hydrogen a batch of the hydrocarbons is contacted at a temperature of 430° – 550° C with a catalyst consisting essentially of a type L zeolite having exchangeable cations of which at least 90% are alkali metal ions selected from the group consisting of ions of sodium, lithium, potassium, rubidium and caesium and containing at least one metal selected from the group which consists of metals of group VIII of the periodic table of elements, tin and germanium, said metal or metals including at least one metal from group VIII of said periodic table having a dehydrogenating effect, so as to convert at least part of the batch into aromatic hydrocarbons.

2. A method according to claim 1, characterised in that the batch of hydrocarbons comprises paraffins containing 6 – 10 carbon atoms, preferably normal paraffins.

3. A method according to claim 1, characterised in that the temperature is between 480° and 520° C.

4. A method according to claim 1, characterised in that the pressure is from 0 to 40 bars.

5. A method according to claim 1, characterised in that the hourly liquid spatial velocity of the hydrocarbons is 0.1 to 20 $h^{-1}$.

6. A method according to claim 1, characterised in that the molar ratio of hydrogen to hydrocarbons is between 2 and 20.

7. A method according to claim 1, characterised in that the metal in group VIII of the periodic table of elements is chosen from the group consisting of platinum and palladium, and the type L zeolite contains from 0.1 to 1.5% by weight thereof.

8. A method according to claim 1, characterised in that at least 90% of the exchangeable cations of the L zeolite are ions of at least one alkali metal chosen from the group consisting of sodium, lithium, potassium, rubidium and caesium.

9. A method according to claim 8, characterised in that the exchangeable cations comprise rubidium and/or caesium.

10. A method according to claim 8, characterised in that potassium ions and caesium ions make up at least 90% of the exchangeable cations.

11. A method according to claim 8, characterised in that potassium ions and rubidium ions make up at least 90% of the exchangeable cations.

12. A method according to claim 9, characterised in that the caesium ions and/or rubidium ions make up at least 30% of the exchangeable cations of the L zeolite.

13. A method according to claim 1, characterised in that the L zeolite contains a metal chosen from the group consisting of platinum and palladium and also contains a metal chosen from the group consisting of rhenium, tin, iridium and germanium, in a proportion such that the total percentage of metals in the zeolite is between 0.1 and 1.5% by weight.

14. A method according to claim 2, characterised in that the temperature is between 480° and 520° C.

15. A method according to claim 4, characterised in that the pressure is from 0 to 25 bars.

16. A method according to claim 15, characterised in that the pressure is from 0 to 25 bars.

17. A method according to claim 1, characterised in that the hourly liquid spatial velocity of the hydrocarbons is between 1 and 4.

18. A method according to claim 4, characterised in that the hourly liquid spatial velocity of the hydrocarbons is between 1 and 4.

19. A method according to claim 1, characterised in that the molar ratio of hydrogen to hydrocarbons is between 2 and 20.

20. A method according to claim 6, characterised in that the molar ratio of hydrogen to hydrocarbons is between 3 and 10.

21. A method according to claim 6, characterised in that the metal in group VIII of the periodic table of elements is chosen from the group consisting of platinum and palladium, and the type L zeolite contains from 0.1 to 1.5% by weight thereof.

22. A method according to claim 7, characterised in that at least 90% of the exchangeable cations of the L zeolite are ions of at least one alkali metal chosen from the group consisting of sodium, lithium, potassium, rubidium and caesium.

23. A method according to claim 10, characterised in that the potassium ions and/or caesium ions make up at least 30% of the exchangeable ions of the L zeolite.

24. A method according to claim 11, characterised in that the potassium ions and/or rubidium ions make up at least 30% of the exchangeable ions of the L zeolite.

25. A method according to claim 1, characterised in that the L zeolite contains a metal chosen from the group consisting of rhenium, tin, iridium and germanium, and also contains a metal other than rhenium and iridium chosen from metals of group VIII of the periodic table of elements, in a proportion such that the total percentage of metals in the zeolite is between 0.1 and 1.5% by weight.

* * * * *